(12) United States Patent
Theil

(10) Patent No.: US 7,096,716 B2
(45) Date of Patent: Aug. 29, 2006

(54) INTEGRATION OF THERMAL REGULATION AND ELECTRONIC FLUID SENSING

(75) Inventor: Jeremy A. Theil, Mountain View, CA (US)

(73) Assignee: Avago Technologies ECBU IP (Singapore) Pte. Ltd., Singapore (SG)

( * ) Notice: Subject to any disclaimer, the term of this patent is extended or adjusted under 35 U.S.C. 154(b) by 58 days.

(21) Appl. No.: 10/981,433

(22) Filed: Nov. 3, 2004

(65) Prior Publication Data

US 2006/0090541 A1 May 4, 2006

(51) Int. Cl.
*G01N 27/02* (2006.01)
*H01L 23/24* (2006.01)
*H01L 21/428* (2006.01)

(52) U.S. Cl. .................. 73/23.34; 73/31.06; 257/414; 438/49

(58) Field of Classification Search .............. 73/23.34, 73/31.05; 257/414; 438/49
See application file for complete search history.

(56) References Cited

U.S. PATENT DOCUMENTS

| | | | |
|---|---|---|---|
| 6,018,187 A | 1/2000 | Theil et al. | |
| 6,495,892 B1 | 12/2002 | Goodman et al. | |
| 6,649,993 B1 | 11/2003 | Theil | |
| 6,759,010 B1 | 7/2004 | Lewis et al. | |

*Primary Examiner*—Daniel S. Larkin

(57) ABSTRACT

A fluid sensor device includes a number of components integrated onto a substrate, such as a semiconductor substrate. The integrated components include analyte-detection transducers, signal processing circuitry for manipulating the signals from the transducers, an elevated interconnect scheme, and thermal regulation capability. The substrate is compatible with the use of integrated circuit fabrication techniques. The interconnect scheme enables dense vias that extend generally perpendicular to the surface of the substrate. The transducers are formed on a planarized side of the interconnect scheme opposite to the substrate. Inkjet printing techniques may be used in locating the transducer materials. Alternatively, the transducers may be photosensitive polymers that polymerize when exposed to light.

17 Claims, 4 Drawing Sheets

INTEGRATION OF THERMAL REGULATION AND ELECTRONIC FLUID SENSING

BACKGROUND ART

Electronic devices that are used to detect gases are sometimes referred to as "electronic noses" or "artificial noses." Similar devices are available for detecting liquids. Possible uses include identifying a presence of an unhealthy environment and identifying constituents of a liquid or gas. Goals in the design of gas-detection and liquid-detection devices include minimizing costs and maximizing reliability and speed.

There are a number of different approaches to detecting and/or identifying fluids (i.e., analytes). One approach is to employ conductive transducers that change electrically when particular molecules are introduced. The electrical change may be with respect to resistance or capacitance. The transducers may be an array of metal oxide pads or chemically absorbent pads which have different specific reactions to analytes. With properly designed arrays, each of a number of different gases will have a unique characteristic set of resistance/capacitance values when the array of transducers is exposed to the gas.

A second general-category approach to designing an electronic nose is to include absorbent polymers in a quartz crystal microbalance (QCM) system. The absorbent polymers will have masses that vary as different molecules are absorbed. As a result, the resonant frequency of the system will change in dependence upon the molecules to which the polymers are exposed. A third approach is similar, since frequency changes are used to identify analytes. In this third approach, a surface acoustic wave (SAW) system is involved, with the frequency variations being with respect to travel along a surface, rather than through a bulk material.

There are at least two optical approaches. In one such approach, the electronic nose includes an array of transducers which are chemically active fluorescent dyes. As analytes interact with the fluorescent dyes, light is generated by the various dyes. The frequencies of the emitted lights are used to identify the gas or gas components. The other optical approach is to utilize dyes which merely change spectral characteristics (color) as a reaction to exposure to fluid molecules.

While the available approaches operate well for their intended purposes, one concern is that sensing results may be influenced by external factors, such as temperature.

SUMMARY OF THE INVENTION

A fluid sensor device in accordance with the invention integrates analyte-detection transducers, signal processing circuitry, an elevated interconnect scheme, and thermal regulation onto a single substrate, so as to improve signal transmission and analyte detection conditions and to reduce the system costs and size. The substrate is compatible with the use of integrated circuit fabrication techniques in the formation of the signal processing circuitry and the interconnect scheme.

The elevated interconnect scheme may comprise electrically insulative material on one side of the substrate and conductive vias through the insulative material to connect the signal processing circuitry to the transducers. The insulative material is planarized, with the vias being substantially perpendicular to the planarized surface.

The transducers are formed on a side of the insulative material opposite to the substrate. If the insulative material is planarized and the ends of the vias are properly exposed, the transducers may be formed directly on the planarized surface. That is, the formation of electrodes or other conductive structures is not necessary in all implementations of connecting the transducers to the vias.

The transducers are formed of materials selected to exhibit electrical properties which vary with respect to at least one of resistance and capacitance when exposed to analytes. Each transducer in a transducer array may be formed of a particular compound having a unique electrical response when exposed to fluid phase molecules. Then, different analytes will exhibit different electrical responses along the transducer array.

In one embodiment, the transducer array is formed using inkjet printing techniques to precisely place polymeric material onto the interconnect scheme. Resistor films may be dissolved in carbon black and the polymeric material to form a solvent, which is deposited using a spin-on approach. Alternatively, by further reducing the viscosity, it is possible to use piezoelectric-based inkjet writing or even thermal inkjet writing techniques to form dots. As an alternative approach, a photosensitive polymer may be formed to break down or polymerize upon exposure to light. Thus, the material may be deposited and then exposed to light to form the final product. Similar chemical systems can be developed in which a photosensitive monomer is inserted into a polymer backbone. An advantage of photolithography is that it is potentially faster and may enable greater uniformity and thickness control.

At least one heater is integrated into the device and is responsive to thermal-regulation signals to provide temperature control. In one embodiment, another integrated component of the substrate-based device is a temperature sensor connected to monitor the temperature of the substrate and to provide an output that is used for dynamically generating the thermal-regulation signal. Regulating the temperature improves the reliability of the analyte detection in many applications. For example, if the transducers are absorbent polymers which vary in mass when exposed to different molecules, the absorbency of the material may change as a function of temperature. Thus, detection results are most likely to remain consistent if the temperature remains consistent. Transducer variations with respect to electrical properties may also be affected by temperature.

DETAILED DESCRIPTION

Figure 1:
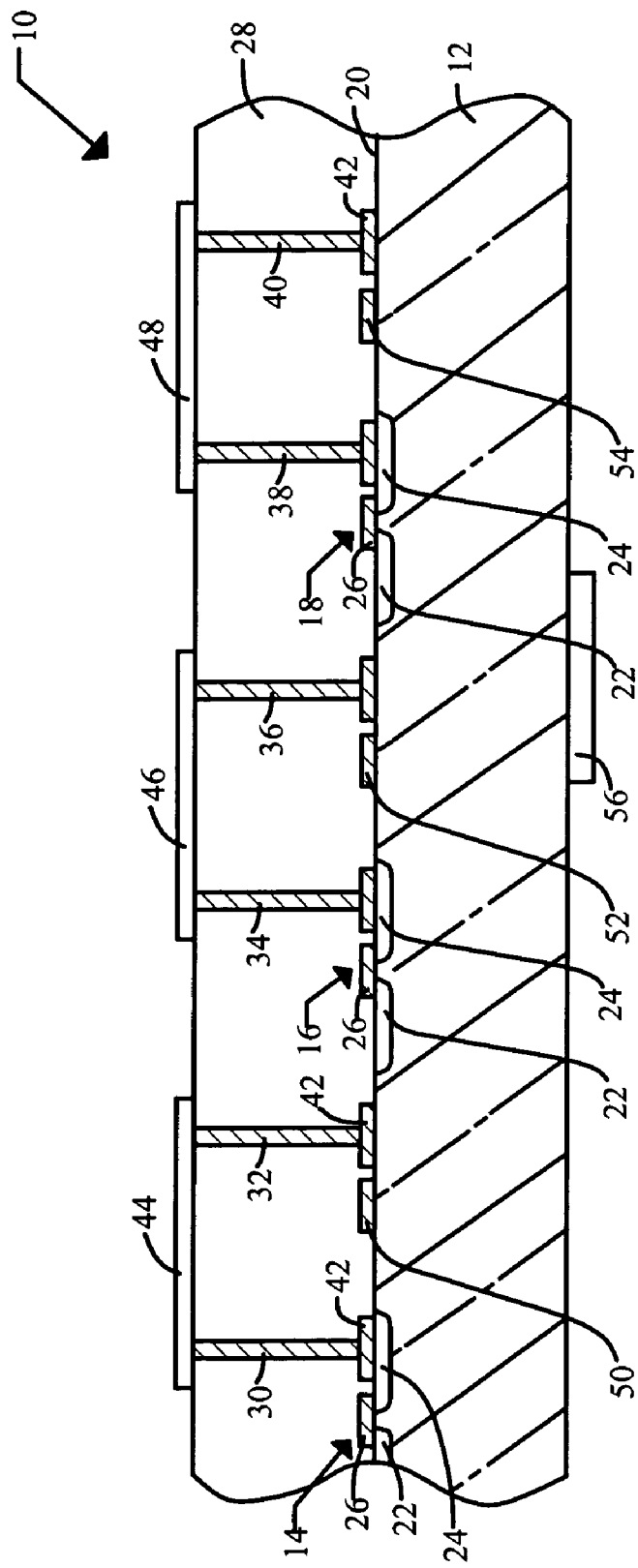
FIG. 1 is a side sectional view of an integrated fluid sensor device in accordance with one embodiment of the invention.

With reference to FIG. 1, one embodiment of a fluid sensor device 10 is shown as including various components integrally formed with a substrate 12 that is compatible with the utilization of integrated circuit fabrication techniques. Typically, the substrate is a semiconductor substrate. A suitable material is silicon. The sensor device enables detection of fluids (i.e., analytes), which may be in the gas phase or the liquid phase.

Integrally formed with the substrate 12 is signal processing circuitry dedicated to manipulating signals for sensing fluids. In FIG. 1, three transistors 14, 16 and 18 are shown on an upper substrate surface 20. Each transistor includes a pair of source/drain regions 22 and 24 and a gate 26. As is well known in the art, the source/drain regions are formed by introducing dopant into the substrate 12, while the gate is formed by patterning conductive material on the substrate surface 20. However, the structures for forming the signal processing circuitry are not exclusively limited to a bipolar approach or to a complementary metal oxide semiconductor (CMOS) approach.

An interconnect scheme is integrally formed on the surface 20 of the substrate 12. The interconnect scheme includes an electrically insulative material 28 through which conductive vias 30, 32, 34, 36, 38 and 40 extend. Optionally, low resistance connections may be provided by traces 42 at the lower ends of the vias.

The interconnect scheme may be fabricated using techniques described in U.S. Pat. Nos. 6,649,993 to Theil and U.S. Pat. No. 6,018,187 to Theil et al., which are assigned to the assignee of the present invention. Spin-on techniques may be employed to coat the upper surface of the substrate 12 with the electrically insulative material 28. Suitable materials include silicon dioxide and silicon nitride ($Si_3N_4$). Alternatively, plasma deposition of Si—O—C—H provides a suitable non-conductive layer. The conductive vias 30–40 extend through the insulative material and electrically connect to intended regions of the signal processing circuitry. Thus, vias 30, 34 and 38 are electrically connected to the source/drain regions 24 of the transistors 14, 16 and 18. On the other hand, the vias 32, 36 and 40 connect to traces 42 that extend along the surface of the substrate to other circuitry components, not shown. The vias may be formed of tungsten, which has the desired step capacity to fill high aspect ratio holes. That is, tungsten can be used to form narrow and relatively long interconnections. The material may be deposited using chemical vapor deposition (CVD) techniques. Other conductive materials which may be used to form the vias include copper and aluminum.

An advantage of the interconnect scheme using vias 30–40 which are substantially perpendicular to the substrate surface 20 is that the interconnected components may be tightly packed. CVD processes allow the formation of generally cylindrical vias having minimal diameters, particularly if the vias are formed of tungsten.

The upper surface of the interconnect scheme is planarized. Thus, the insulative material 28 and the ends of the vias 30–40 provide a flat surface for depositing transducers 44, 46 and 48. Each transducer is formed of a material having properties which vary when exposed to analytes. Particular fluids can be identified by using multiple transducer elements that have highly variable specificity to fluids. The variation may be with respect to resistance or capacitance, but other electrical-related properties may be targeted in providing transducers which detect fluids. Unique patterns of specificities may be used to identify a range of particular species, or even a small number of species simultaneously. Suitable transducer materials include conductive polymers, conductive polymer composites, metalloporyphins, conductive oxide film resistors, polymer quartz crystal microbalance (QCM) systems, and the like.

As shown in FIG. 1, each transducer 44, 46 and 48 is connected to a pair of vias 30–40. Thus, the vias are able to bias the transducers and/or monitor the electrical properties of the transducers.

A concern is that the temperature of the fluid sensor device 10 or specific components of the device may be susceptible to changes in operation as a function of temperature. For example, if the transducers 44, 46 and 48 are chemically absorbent pads with electrical properties that vary as particular molecules are absorbed, it is important that the absorbency properties of the pads remain relatively fixed if the device is to operate as designed. Therefore, heaters 50, 52 and 54 are integrated into the device 10. While three separate heaters are shown in FIG. 1, a single heater may be used in some applications. As one possibility, the heaters 50, 52 and 54 are portions of a serpentine resistive pattern formed on the substrate surface 20 in order to provide a uniformity of temperature. However, some embodiments may include separately controlled heaters in order to minimize the likelihood of temperature gradients from one transducer 44, 46 and 48 to the next.

In the embodiment of FIG. 1, a temperature sensor 56 is integrated onto the bottom surface of the substrate 12. As another possibility, the temperature sensor may be formed on the same surface 20 as the heaters 50, 52 and 54. The temperature sensor may be a diode that detects temperature as a function of changes in thermal leakage. However, other possibilities are available.

Figure 2:
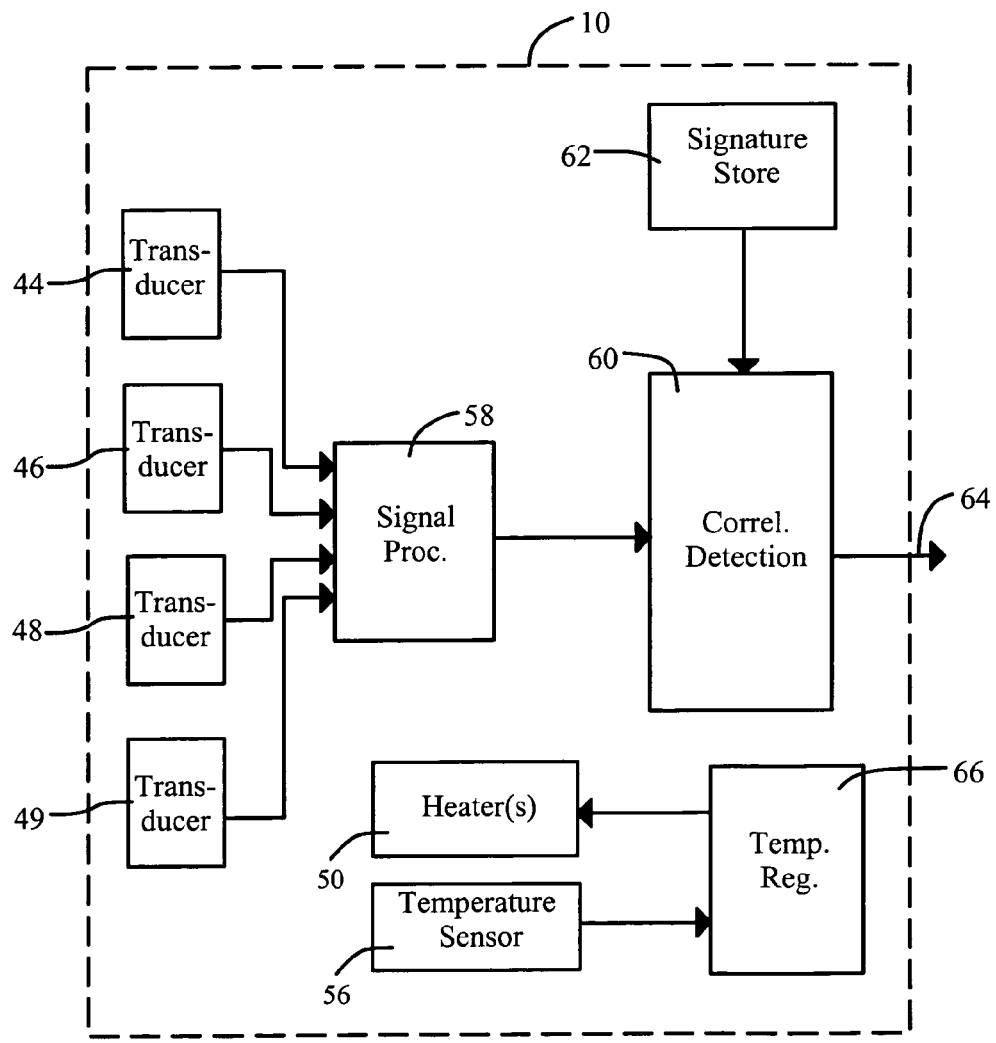
FIG. 2 is a block diagram of components of the integrated fluid sensor device of FIG. 1.

Referring now to FIG. 2, the fluid sensor device 10 is shown as including the three transducers 44, 46 and 48, as well as a fourth transducer 49. The optimal arrangement of transducers will depend upon the intended application of the device 10. The dashed lines in FIG. 2 are intended to indicate that the enclosed components are integrated, rather than some of the components being housed within a second integrated circuit package or being otherwise externally located.

The outputs of the transducers 44, 46, 48 and 49 are connected to signal processing circuitry 58 dedicated to manipulating signals for sensing fluids. The circuitry may include analog-to-digital converters, transducerbiasing components, and/or monitoring components for providing a reading specific to each current condition of each transducer.

The signal processing circuitry 58 is connected to a correlation detection circuit 60. The fluid sensor device 10 may include a signature store component 62 (on-chip memory) that may include a database of different sequences of transducer readouts, with each sequence being associated with a particular fluid. When the correlation detection circuit recognizes a correlation between a sequence within the signature store and the current condition of the transducers 44, 46, 48 and 49, an output is generated that indicates the recognized fluid. In FIG. 1, an output connection 64 may be used to conduct the information to external circuitry, not shown.

The heater 50 or heaters and the temperature sensor 56 are connected to a temperature regulation circuit 66. In the illustrated embodiment, both the temperature sensor and the temperature regulation circuit are on-chip components. However, other embodiments may provide the circuitry off-chip.

In operation, the temperature sensor 56 monitors the current temperature of the fluid sensor device 10. The output of the sensor is connected to the temperature regulation circuit 66. In turn, the circuit has an output connected to the heater 50 or heaters. A thermal-regulation signal dynamically controls the power to each heater in order to maintain the transducers 44, 46, 48 and 49 in a condition to provide consistent results.

Figure 3:
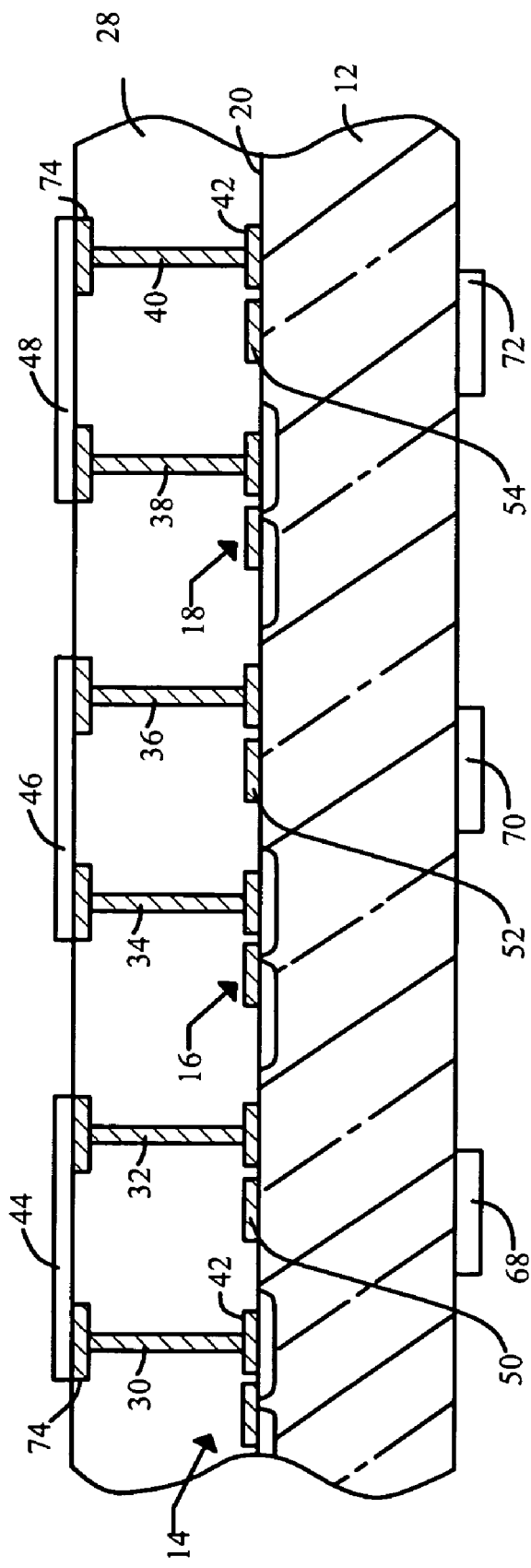
FIG. 3 is a side sectional view of a second embodiment of an integrated fluid sensor device in accordance with the invention.

FIG. 3 illustrates a second embodiment of the invention. In this embodiment, each heater 50, 52 and 54 is associated with a dedicated temperature sensor 68, 70 and 72. As a result, temperature gradients along the surface 20 of the substrate 12 can be avoided. In another embodiment, the temperature sensors are adjacent to the heaters and are along the substrate surface 20.

Another structural difference between the embodiment of FIG. 1 and the embodiment of FIG. 3 is the use of low resistance contacts 74 at the upper ends of the vias 30–40. These contacts may be formed of the same material as the traces 42 at the lower ends of the vias. In fabrication, the insulative material 28 may be patterned after the formation of the vias, so as to provide trenches to receive the conductive material used for the contacts 74. As in the embodiment of FIG. 1, the top surface of the insulative material is planarized, so that the transducers 44, 46 and 48 are fabricated on a flat surface.

Figure 4:
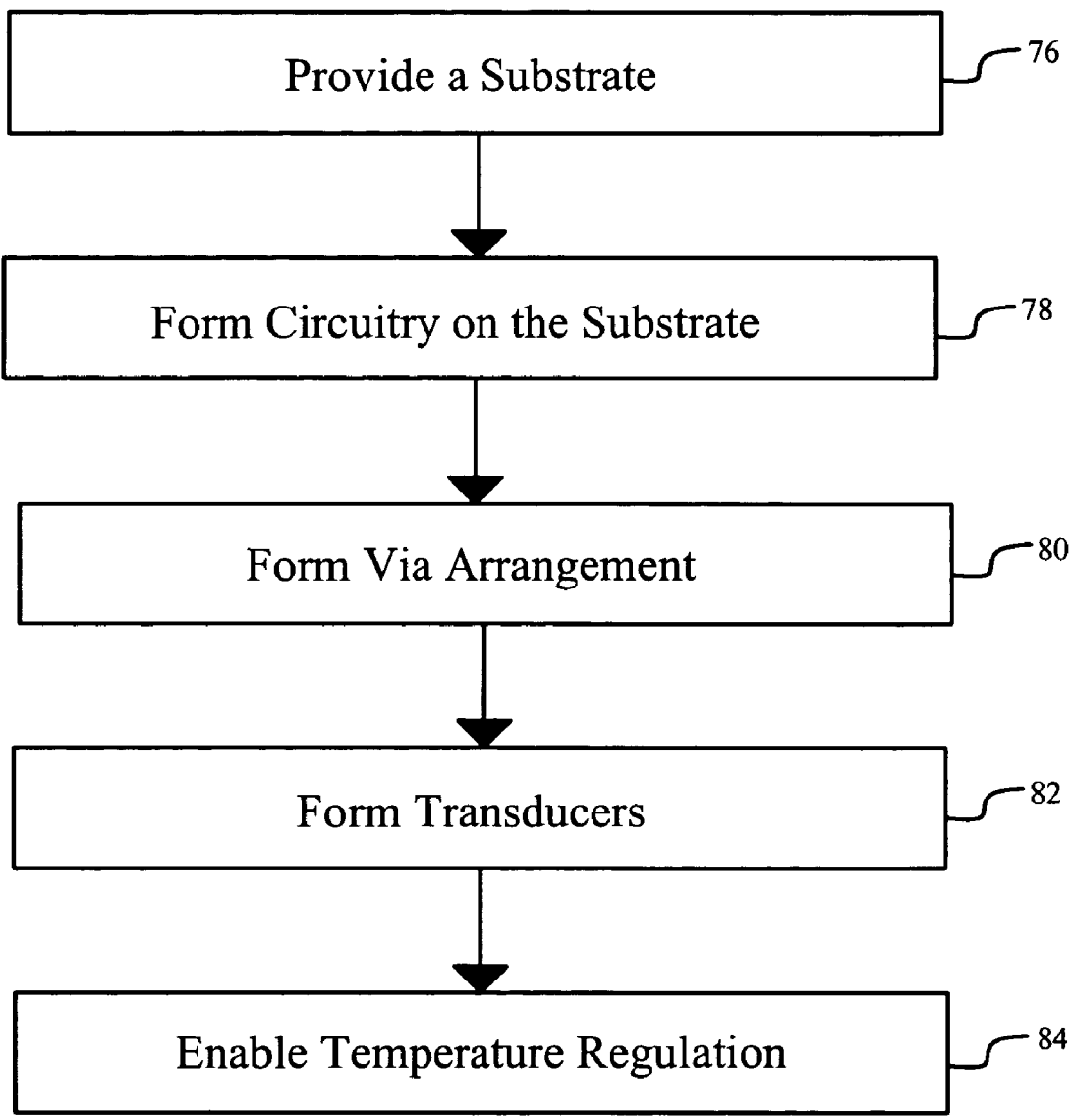
FIG. 4 is a process flow of steps for fabricating the integrated fluid sensor device of FIG. 1 or 3.

Referring now to FIG. 4, a process flow of steps includes providing the substrate 76 to which the various components of the fluid sensor device are to be integrated. The selection of the substrate is based upon compatibility with the use of the desired integrated circuit fabrication techniques. A suitable material is silicon.

At step 78, circuitry is formed on the substrate. Integrated circuit fabrication techniques are employed to provide on-chip components. The circuitry includes a circuit for processing signals that are indicative of particular fluids. The fluids may be in the gaseous phase or the liquid phase, depending upon the selection of transducers and the intended application.

A via arrangement is formed at step 80. An advantage of the interconnect scheme shown in FIGS. 1 and 3 is that the vias 30–40 and the fluid-sensing circuitry can be densely packed. Moreover, the surface of the insulative material 28 opposite to the substrate 12 is planarized. However, it is unnecessary to form electrodes prior to forming the transducers 44, 46 and 48.

The formation of the transducers 44, 46 and 48 at step 82 may be by means similar to those used for inkjet printing. The polymer can be precisely placed relative to a semiconductor die using inkjet printing techniques. One common approach for producing an appropriate film is to dissolve carbon black and the polymer into a solvent which can be spun-on. By further reducing the viscosity, it is possible to use piezoelectric-based inkjet writing. Thermal inkjet writing to form dots is also a possibility.

An alternative transducer fabrication approach is to develop a photosensitive polymer that breaks down or polymerizes upon exposure to light. Similar chemical systems can be developed in which a photosensitive monomer is inserted into the polymer backbone.

In step 84 of FIG. 4, the temperature regulation is enabled. At least one heater is formed on the substrate provided in step 76. Preferably, the integrated fluid sensor device also includes a temperature sensor, so that thermal-regulation signals can be dynamically generated in order to stabilize the temperature.

What is claimed is:

1. An integrated fluid sensor device comprising:
   a substrate;
   signal processing circuitry integrally formed with said substrate, said signal processing circuitry including circuitry dedicated to manipulating signals for sensing fluids;
   electrically insulative material having conductive vias extending therethrough, said electrically insulative material residing at one side of said substrate, said vias being in communication with said signal processing circuitry;
   transducers at ends of said vias opposite to said substrate to generate said signals for sensing fluids, said transducers having properties which are varied when exposed to said fluids; and
   a heater integrally formed with said substrate, said heater being connected to be responsive to thermal-regulation signals to provide temperature control.

2. The device of claim 1 wherein said vias are substantially perpendicular to said side of said substrate on which said electrically insulative material resides.

3. The device of claim 1 wherein a surface of said electrically insulative material opposite to said substrate is planar, said transducers being positioned on said surface in contact with said surface and said vias.

4. The device of claim 3 wherein each said transducer is formed of a material selected to exhibit electrical properties which vary with respect to at least one of resistance and capacitance when exposed to said fluids.

5. The device of claim 4 wherein said transducers are formed of different said materials that are selected to vary with respect to one of resistance and capacitance, each said transducer being a homogeneous structure in direct contact with an associated said via.

6. The device of claim 1 further comprising a temperature sensor connected to monitor the temperature of said substrate, said temperature sensor being configured to provide an output for dynamically generating said thermal-regulation signals.

7. A method of fabricating a fluid sensor device comprising:
   providing a substrate;
   forming circuitry on said substrate using integrated circuit fabrication techniques, including forming circuitry for processing signals that are indicative of fluids;
   forming a via arrangement on said circuitry, said via arrangement including an insulating material having conductive vias extending from said circuitry to an upper surface of said via arrangement, said upper surface being planarized;
   forming transducers on said planarized upper surface in contact with said vias, said transducers being specific to sensing fluids; and
   integrating temperature regulation into said substrate to dynamically thermal conditions for sensing said fluids, including forming heater elements that are responsive to thermal-regulation signals.

8. The method of claim 7 wherein forming said transducers includes depositing photosensitive polymers on said planarized upper surface and exposing said photosensitive polymers to light to chemically stabilize said photosensitive polymers.

9. The method of claim 7 wherein forming said transducers includes dissolving carbon black and fluid sensing material into a solvent and includes using inkjet printing techniques.

10. The method claim 9 wherein using said inkjet printing techniques includes employing a piezoelectric-based approach.

11. The method of claim 7 wherein integrating said temperature regulation includes employing integrated circuit fabrication techniques to pattern resistive material so as to define said heater elements.

12. The method of claim 11 wherein integrating said temperature regulation further includes forming a temperature sensor in thermal contact with said substrate to monitor current temperature of said substrate.

13. The method of claim 12 further comprising providing connections to said temperature sensor and said heater elements to enable feedback control of said current temperature.

14. A fluid sensor system comprising:
a sensor device that includes signal processing circuitry and at least one heater integrated with a semiconductor substrate, said sensor device further including a temperature sensor for monitoring a current temperature of said sensor device, said sensor device having a via arrangement formed on said substrate, said via arrangement including an insulating material, a planarized upper surface and conductive vias that are perpendicular to said planarized upper surface, said sensor device having fluid-identification transducers in direct contact with said vias, said transducers being on said planarized upper surface;
thermal feedback circuitry having an input connected to said temperature sensor and having an output connected to each said heater to regulate said current temperature; and
fluid identification circuitry connected to said signal processing circuitry to enable fluids contacting said transducers to be identified.

15. The system of claim 14 wherein each transducer is formed of a homogeneous material in contact with one of said vias and wherein different said transducers are formed of different said homogeneous materials.

16. The system of claim 14 wherein said signal processing circuitry of said sensor device is enabled to distinguish different fluids and to output first level identification information to said fluid identification circuitry.

17. The system of claim 14 wherein said transducers have electrical properties which vary when exposed to fluids.

* * * * *